US010634658B2

(12) United States Patent
Hall

(10) Patent No.: US 10,634,658 B2
(45) Date of Patent: Apr. 28, 2020

(54) SELECTIVE ANALYSIS OF MODIFIED BIOLOGICAL MOLECULES WITH SOLID-STATE NANOPORES

(71) Applicant: WAKE FOREST UNIVERSITY HEALTH SCIENCES, Winston-Salem, NC (US)

(72) Inventor: Adam R. Hall, Clemmons, NC (US)

(73) Assignee: WAKE FOREST UNIVERSITY HEALTH SCIENCES, Winston-Salem, NC (US)

(*) Notice: Subject to any disclaimer, the term of this patent is extended or adjusted under 35 U.S.C. 154(b) by 0 days.

(21) Appl. No.: 15/310,630

(22) PCT Filed: May 13, 2015

(86) PCT No.: PCT/US2015/030531
§ 371 (c)(1),
(2) Date: Nov. 11, 2016

(87) PCT Pub. No.: WO2015/175638
PCT Pub. Date: Nov. 19, 2015

(65) Prior Publication Data
US 2017/0082599 A1    Mar. 23, 2017

Related U.S. Application Data

(60) Provisional application No. 61/992,814, filed on May 13, 2014, provisional application No. 62/132,989, filed on Mar. 13, 2015.

(51) Int. Cl.
*G01N 33/487* (2006.01)

(52) U.S. Cl.
CPC ............................. *G01N 33/48721* (2013.01)

(58) Field of Classification Search
CPC ........ C12Q 2522/101; C12Q 2565/631; G01N 33/48721; G01N 27/447
See application file for complete search history.

(56) References Cited

U.S. PATENT DOCUMENTS

2006/0073489 A1* 4/2006 Li ......................... B01D 57/02
                                                           435/6.11
2006/0210995 A1* 9/2006 Joyce .................... B82Y 15/00
                                                           435/6.12

(Continued)

FOREIGN PATENT DOCUMENTS

WO    WO/2013/012881 A2 †  1/2013
WO    WO-2013016486 A1 *   1/2013 ........... C12Q 1/6827

(Continued)

OTHER PUBLICATIONS

U.S. Appl. No. 61/839,328, filed Jun. 25, 2013 (Year: 2013).*

(Continued)

*Primary Examiner* — Betty J Forman
(74) *Attorney, Agent, or Firm* — J. Clinton Wimbish; Nexsen Pruet PLLC

(57) ABSTRACT

In one aspect, methods are described herein for the selective detection and quantitative analysis of biological molecule compositions. A method described herein comprises providing a mixture comprising biological molecules, such as DNA, RNA or proteins, complexed with a translocating agent, such as another DNA or protein, and non-complexed biological molecules. The mixture is contacted with a membrane comprising at least one nanopore and an electric field is applied across the nanopore to selectively translocate the biological molecules complexed with the translocating agent through the at least one nanopore. Concentration of the complexed biological molecules is determined based on the translocation rate of said molecules.

19 Claims, 9 Drawing Sheets

(56) References Cited

U.S. PATENT DOCUMENTS

| | | | | |
|---|---|---|---|---|
| 2008/0025875 | A1* | 1/2008 | Martin | B01D 67/0032 422/82.01 |
| 2012/0288948 | A1* | 11/2012 | Lindsay | G01N 33/48721 436/94 |
| 2013/0109577 | A1* | 5/2013 | Korlach | G01N 27/3278 506/4 |
| 2014/0174927 | A1* | 6/2014 | Bashir | C12Q 1/6827 204/452 |
| 2014/0378331 | A1* | 12/2014 | Morin | G01N 33/48721 506/9 |

FOREIGN PATENT DOCUMENTS

| | | | |
|---|---|---|---|
| WO | WO/2014/182634 | A1 † | 11/2014 |
| WO | WO/2014/210219 | A1 † | 12/2014 |

OTHER PUBLICATIONS

Kowalczyk et al "Detection of local protein structures along DNA using solid-state nanopores" Nano Letters, 2009, 10: 324-328. (Year: 2009).*

International Search Report and Written Opinion issued in corresponding International Application No. PCT/US2015/030531 dated Jul. 21, 2015, 11 pages.

Wanunu, M. et al., "Nanopore Analysis of Individual RNA/ Antibiotic Complexes", ACS Nano, vol. 5, No. 12, Dec. 27, 2011, pp. 9345-9353, XP055201578.

Larkin, Joseph et al., "High-Bandwidth Protein Analysis Using Solid-State Nanopores", Biophysical Journal, vol. 106, No. 3, Feb. 28, 2014, pp. 696-704, XP028606798.

Niedzwiecki David J. et al., Sampling a Biomarker of the Human Immunodeficiency Virus across a Synthetic Nanopore, ACS Nano, vol. 7, No. 4, Apr. 23, 2013, pp. 3341-3350, XP055201569.

Chu, John et al., "Real-Time Monitoring of DNA Polymerase Function and Stepwise Single-Nucleotide DNA Strand Translocation through a Protein Nanopore", Angewandte Chemie (International Ed. in English), vol. 122, No. 52, Nov. 23, 2010, pp. 10304-10307, XP055148678.

Wanunu, M., et al., "Electrostatic focusing of unlabelled DNA into nanoscale pores using a salt gradient", Nature Nanotechnology, vol. 5, No. 2, Dec. 20, 2009, pp. 160-165, XP055134839.

\* cited by examiner
† cited by third party

SELECTIVE ANALYSIS OF MODIFIED BIOLOGICAL MOLECULES WITH SOLID-STATE NANOPORES

RELATED APPLICATION DATA

This application is a U.S. National Phase of PCT/US2015/030531, filed May 13, 2015, which claims priority pursuant to 35 U.S.C. § 119(e) to U.S. Provisional Patent Application Ser. No. 61/992,814 filed May 13, 2014 and U.S. Provisional Application Ser. No. 62/132,989 filed Mar. 13, 2015, each of which is incorporated herein by reference in their entireties.

FIELD

The present invention relates to the analysis of biological molecule compositions and, in particular, to the selective detection and quantification of biological molecule compositions with solid state nanopores.

BACKGROUND

Immunoprecipitation and pull-down assays are workhorses in biochemistry. With the ability to discriminate specific substrates in heterogeneous mixtures, they play important roles in a wide range of fields, including proteomics, epigenomics and transcriptomics. However, despite their broad utility, these well-established strategies have limitations. Besides requiring large sample sizes, they are labor-intensive and are not inherently quantitative, typically requiring subsequent PCR or enrichment for downstream analysis. For these reasons, quantitative technologies with single-molecule sensitivity may offer important advantages.

SUMMARY

In one aspect, methods are described herein for the selective detection and quantitative analysis of biological molecule compositions. A method described herein comprises providing a mixture comprising biological molecules complexed with a translocating agent and non-complexed biological molecules. The mixture is contacted with a membrane comprising at least one nanopore and an electric field is applied across the nanopore to translocate the biological molecules complexed with the translocating agent through the at least one nanopore, wherein translocation of the complexed biological molecules is selectively detected. In some embodiments, a method described herein further comprises measuring change in current through the nanopore during one or more translocation events of the complexed biological molecules. Moreover, the method can further comprise measuring the rate of translocation events of the complexed biological molecules and determining concentration of the complexed biological molecules from the rate of translocation events. Importantly, the translocated complexed biological molecules can be recovered from solution and are thereby separated from the non-complexed biological molecules of the initial mixture. Biological molecules suitable for analysis according to methods described herein include nucleic acids and proteins. In some embodiments, for example, the biological molecules include single-stranded and double stranded dexoxyribonucleic acid (DNA) as well as ribonucleic acid (RNA) and RNA having intra-strand double helices.

These and other embodiments are described in greater detail in the detailed description which follows.

DETAILED DESCRIPTION

Figure 1:
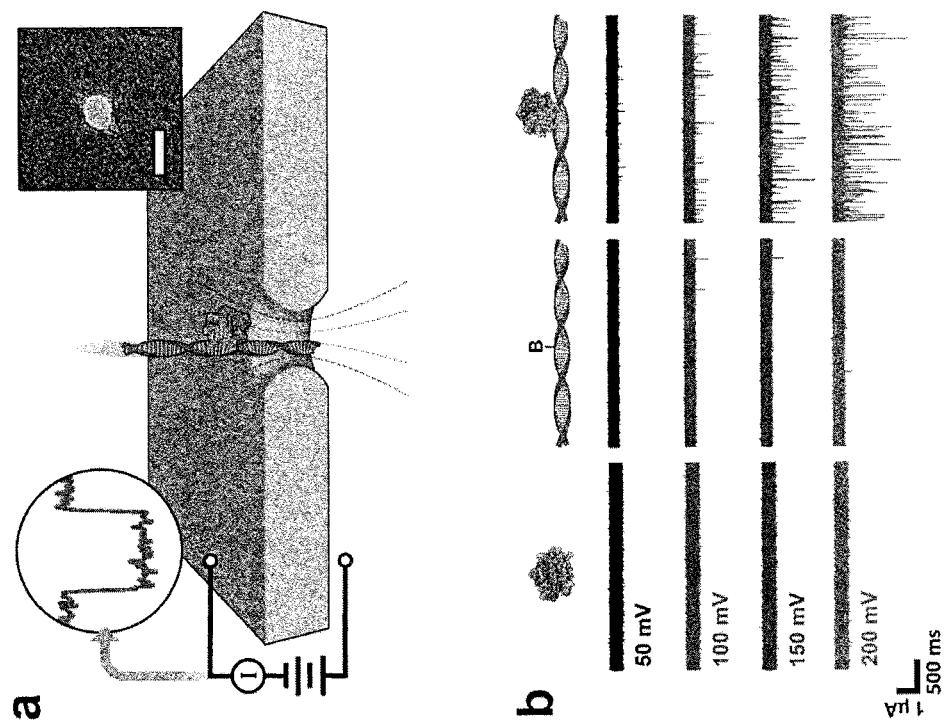
FIG. 1 illustrates a method of biological molecule composition analysis according to one embodiment described herein.

Embodiments described herein can be understood more readily by reference to the following detailed description and examples and their previous and following descriptions. Elements, apparatus and methods described herein, however, are not limited to the specific embodiments presented in the detailed description and examples. It should be recognized that these embodiments are merely illustrative of the principles of the present invention. Numerous modifications and adaptations will be readily apparent to those of skill in the art without departing from the spirit and scope of the invention.

In one aspect, methods are described herein for the selective detection and quantitative analysis of biological molecule compositions. A method described herein comprises providing a mixture comprising biological molecules complexed with a translocating agent and non-complexed biological molecules. The mixture is contacted with a membrane comprising at least one nanopore and an electric field is applied across the nanopore to translocate the biological molecules complexed with the translocating agent through the at least one nanopore, wherein translocation of the complexed biological molecules is selectively detected. In some embodiments, a method described herein further comprises measuring change in current through the nanopore during one or more translocation events of the complexed biological molecules. Moreover, the method can further comprise measuring the rate of translocation events of the complexed biological molecules and determining concentration of the complexed biological molecules from the rate of translocation events. Importantly, the translocated complexed biological molecules can be recovered from solution and are thereby separated from the non-complexed biological molecules of the initial mixture.

Turning now to specific steps, a method described herein comprises providing a mixture including biological molecules complexed with a translocating agent and non-complexed biological molecules. Any biological molecule not inconsistent with the objectives of the present invention can be selectively detected and quantified according to methods described herein. Biological molecules suitable for analysis according to methods described herein include nucleic acids. In some embodiments, for example, biological molecules include ss-DNA, ds-DNA as well as RNA and RNA having intra-strand double helices. RNA can include mRNA, miRNA, rRNA, tRNA, tmRNA, aRNA or mixtures thereof. Nucleic acids can have any desired number of nucleotides not inconsistent with the objectives of the present invention. In some embodiments, for example, a nucleic acid for analysis has 25 to 1000 nucleotides. Additionally, a nucleic acid can have a number of nucleotides selected from Table I.

TABLE I

| Nucleic Acid Length Nucleotides |
| --- |
| 100-600 |
| 200-500 |
| 250-400 |
| 50-300 |
| 100-200 |
| 1-500 |

Nucleic acids of the mixture can be derived from eukaryotic, prokaryotic and/or viral sources. Further, biological molecules can include nucleic acid fragments or oligonucleotides. Oligonucleotides of any length not inconsistent with the objectives of the present invention can be selectively detected and quantified according to methods described herein. Further, a biological molecule for analysis can include single nucleotides and/or derivatives thereof.

In addition to nucleic acids, biological molecules suitable for analysis according to methods described herein include proteins. Any protein not inconsistent with the objectives of the present invention can be employed in methods described herein.

As described herein, biological molecules of the mixture are selectively complexed with a translocating agent. A translocating agent is chemical species of sufficient charge and/or structure to permit selective detection of translocation of the complexed biological molecule with the applied electric field set by an applied voltage. In some embodiments, for example, the translocating agent is a biological molecule, including a protein, nucleic acid or nucleic acid fragment. The biological molecule can be in a naturally occurring state. Alternatively, the biological molecule can be modified to demonstrate specific binding, suitable electric charge and/or structure to permit selective detection of complexed biological molecule translocation. In some embodiments, a translocating agent includes a single strand nucleic acid modified with an affinity tag for binding one or more molecular species prior translocation of the complexed biological molecule. For example, a translocating agent can comprise a single strand nucleic acid of known specific sequence, wherein the single strand nucleic acid is modified with a protein tag. The protein tag can bind suitable protein in the mixture of biological molecules prior to translocation of the biological molecule complexed with the translocation agent. In one embodiment, a translocating agent of single strand nucleic acid is biotinylated for binding streptavidin prior to translocation of the target nucleic acid of complimentary sequence.

In other embodiments, a translocating agent is a non-biological chemical species, such as a nanoparticle. Any nanoparticle not inconsistent with the objectives of the present invention can be employed. Nanoparticles, for example, can comprise organic nanoparticles including carbon nanoparticles (carbon nanotubes, graphene, fullerenes, etc.). Nanoparticles can also include inorganic nanoparticles such as semiconductor nanoparticles, ceramic nanoparticles and/or metal nanoparticles.

Translocating agent is added to the biological molecule mixture, and the translocating agent selectively binds biological molecules to provide the complexed biological molecules. Biological molecules not selectively bound by the translocating agent form the non-complexed biological molecules of the mixture.

For complexing the biological molecule for selective translocation detection, the translocating agent can comprise a site specific binding region. Depending on the identity of the biological molecule to be complexed, the site specific binding region can be a DNA or RNA binding domain. For example, in some embodiments, a translocating agent can bind directly to a nucleic acid warranting use of a nucleic acid binding domain.

Single strand nucleic acid translocating agent can selectively hybridize with a target single strand nucleic acid of complimentary sequence in the mixture of biological molecules. Selective hybridization followed by translocation can permit quantification of the target single strand nucleic acid in the mixture. In some embodiments, multiple single strand nucleic acid translocating agents of differing sequences can be used to identify the presence and/or quantify several target single strand nucleic acids in the mixture. Highly conserved sequences, for example, can be employed in translocating agents permitting identification of specific species in the mixture, such as various bacterial species. Homology could also be monitored where mismatch of one or more base pairs are registered in the analytical results. Further, DNA melting and/or annealing characteristics can be elucidated by employing single strand nucleic acid translocating agents. Transition between the single strand form (uncomplexed with translocating agent) and double stranded form (complexed with translocating agent) can be temporally correlated with translocation events.

Alternatively, the site specific binding region can be a protein binding domain. In other embodiments, the nucleic acid can be provided an affinity tag for binding the translocating agent, thereby warranting a protein binding domain.

A translocating agent can permit selective detection of complexed biological molecule translocation by several mechanisms depending on identity of the complexed biological molecule. In some embodiments, for example, the biological molecule of interest is not of sufficient charge to translocate through the nanopore at the selected conditions of applied electric field and/or other solution conditions. In such embodiments, the translocating agent provides the biological molecule of interest sufficient charge to undergo translocation at the selected applied electric field and/or other solution conditions. Therefore, translocation of the complexed biological molecule can be selectively detected as the non-complexed biological molecules of the mixture do not translocate under the selected conditions.

Alternatively, the biological molecule of interest is of high charge and undergoes translocation at a rate undetectable with conventional electronics employed in nanopore analysis. Proteins, for example, often translocate at rates undetectable by conventional electronics, thereby rendering nanopore apparatus unsuitable for protein detection and quantification. In such embodiments, the translocating agent can be of sufficient opposite charge and/or size to retard the protein translocation rate for detection and quantification by conventional nanopore systems and electronics. Similarly, single strand nucleic acids often translocate at rates undetectable by conventional electronics, thereby rendering the nanopore apparatus unsuitable for nucleic acid detection and quantification. In such embodiments, single strand nucleic acid translocating agent having sequence complimentary to a single strand nucleic acid target in the mixture of biological molecules is employed. The single strand nucleic acid translocating agent exhibits structure permitting detection of the complex formed with the target single strand nucleic acid. As described herein, the single strand nucleic acid translocating agent can be modified with an affinity tag, such as a protein tag, for binding one or more molecular species prior translocation of the complexed target single strand nucleic acid. Further, the translocation agent may provide a translocation rate or nanopore dwell time that can be sufficiently differentiated from other species in the mixture.

As described herein, the mixture comprising biological molecules complexed with the translocating agent and non-complexed biological molecules is contacted with a membrane comprising at least one nanopore. In some embodiments, the membrane comprises an array of nanopores. The membrane can have any thickness and be formed from any material not inconsistent with the objectives of the present invention. In some embodiments, a membrane is non-metallic. A non-metallic membrane can comprise one or more electrically insulating materials, including ceramic materials. Suitable ceramics include metal oxides, metal nitrides, metal carbides or metal carbonitrides or combinations thereof. In some embodiments, a ceramic suitable for use as a membrane is silicon nitride (SiN, $Si_3N_4$). Additionally, a membrane ceramic can comprise silicon oxide, silicon carbide, aluminum oxide or a transition metal oxide.

In some embodiments, a ceramic membrane is polycrystalline in nature. In some embodiments, a ceramic membrane is single crystalline in nature. Moreover, a ceramic membrane can be multilayered. Individual layers of a multilayered membrane can comprise the same material or divergent materials. In some embodiments, individual layers of a ceramic membrane are independently selected from the group consisting of transition metal carbide, transition metal nitride, transition metal carbonitride, transition metal oxide, alumina, silica and silicon nitride.

Further, a membrane can comprise one or more semiconducting materials. In some embodiments, suitable semiconducting materials include II/VI semiconductors, Group IV semiconductors or III/V semiconductors. In some embodiments, a semiconductor material comprises a ternary semiconductor or a quaternary semiconductor. Suitable semiconductor materials can have an amorphous structure, crystalline structure or mixture thereof. Crystalline semiconductor materials can be polycrystalline or single crystalline.

In some embodiments, a membrane is metallic. In such embodiments, a membrane can be a metal or various alloys of metals. In some embodiments, for example, suitable metals are transition metals, including noble metals such as gold. Alternatively, a membrane, in some embodiments, is not gold. Metallic membranes can be coated with dielectric or electrically insulating materials for use in methods described herein.

In some embodiments, a membrane comprises an organic material. For example, a membrane can comprise one or more polymeric materials. Suitable polymeric materials include thermoplastics, thermosets or elastomers. A polymeric material, in some embodiments, comprises one or more of polyethylene, polypropylene, and polycarbonate.

Membranes suitable for use methods described herein can have any desired thickness. In some embodiments, a membrane has a thickness suitable for detecting and/or conducting analysis of one or more nucleic acid segments, including single-strand nucleic acid segments. In some embodiments, a membrane has an average thickness less than about 200 nm or less than about 100 nm. In some embodiments, a membrane has an average thickness according to Table II.

TABLE II

| Nanopore Membrane Thicknesses (nm) |
| --- |
| Membrane Thickness (nm) |
| <50 |
| 1-30 |
| 10-20 |
| 20-50 |
| 50-100 |
| 100-500 |
| 250-750 |

Further, a membrane can have a thickness on the atomic scale. In some embodiments, a membrane has a thickness less than 1 nm, such as 0.1 nm to 0.9 nm. In some embodiments, the thickness of a membrane is measured prior to nanopore formation according to a method described herein.

In addition, a nanopore of a membrane described herein can have any size and shape not inconsistent with the objectives of the present invention. In some embodiments, for example, at least one nanopore has a diameter greater than about 1 nm or greater than about 5 nm. A nanopore of a membrane described herein can have a diameter according to Table III.

TABLE III

| Nanopore Diameter (nm) |
| --- |
| Nanopore Diameter |
| >10 |
| 1-20 |
| 1-10 |
| 1-5 |
| 5-10 |
| 10-15 |
| 10-20 |
| 1.5-4 |

Further, a nanopore can have a thickness commensurate with the average thickness of the membrane. Therefore, in some embodiments, a nanopore can have a thickness selected from Table II herein. Alternatively, a nanopore has a thickness less than the average thickness of the membrane.

Moreover, the diameter and/or thickness of a nanopore can be selected based on a desired signal to noise ratio (SNR) of a measurement described herein, such as a current measurement associated with a translocation event. The SNR of a translocation event, in some embodiments, is higher for larger diameter nanopores and lower for smaller diameter nanopores. Additionally, in some embodiments, the diameter and/or thickness of a nanopore are selected based on a desired dwell time of a translocated species in the nanopore or a desired duration of a translocation event. In some embodiments, the dwell time and/or the duration of a translocation event is longer for a thicker nanopore than for a thinner nanopore. Dwell time, in some embodiments, is the time elapsed from an initial conductance drop in the nanopore until its return to the baseline value.

A membrane described herein can be formed in any manner not inconsistent with the objectives of the present invention. In some embodiments, for instance, a membrane is formed according to a method described in Patent Cooperation Treaty (PCT) Application Publication WO 2012/170499, the entirety of which is hereby incorporated by reference.

As described herein, an electric field is applied across the nanopore to translocate the biological molecules complexed with the translocating agent through the at least one nanopore, wherein the translocation events are selectively detected. The electric field can be set according to any applied voltage not inconsistent with the objectives of the present invention. Suitable applied voltages, for example can range from 1 mV to 5 V. In some embodiments, the applied voltage ranges from 10 mV to 1 V or 50 mV to 500 mV.

In some embodiments, a method described herein further comprises measuring change in current through the nanopore during one or more translocation events of the complexed biological molecules. Moreover, the method can further comprise measuring the rate of translocation events of the complexed biological molecules and determining concentration of the complexed biological molecules from the rate of translocation events. In some embodiments, for example, concentration of the complexed biological molecules Importantly, the translocated complexed biological molecules can be recovered from solution and are thereby separated from the non-complexed biological molecules of the initial mixture.

These and other embodiments are further illustrated in the following non-limiting examples.

Example 1

Selective Detection and Quantification Double-Stranded DNA

Selective detection and quantification of ds-DNA modified with biotin for binding a monovalent streptavidin (MS) translocating agent is detailed in this example. SS-nanopore discrimination of monobiotinylated ds-DNA employed in this example is illustrated in FIG. 1. In FIG. 1a, an electrical bias is applied across a thin-film membrane with a single nanopore immersed in electrolyte solution. This facilitates the electrokinetic translocation of molecules (or molecular complexes) through the pore, each of which can produce an ionic current event. This technique was used to measure MS (FIG. 1b left) and monobiotinylated 90 by ds-DNA (bio90, FIG. 1b center) individually at concentrations of 8 µM and 1 µM, respectively. Over a range of 50-200 mV, few events were identified for either molecule. However, when MS and bio90 are incubated together at a molar ratio of 8:1 (MS: bio90) prior to measurements, a remarkable increase in the number of translocation events per unit time (FIG. 1b right) was observed. The event rate of the admixture was consistently more than an order of magnitude greater than that of either constituent molecule alone; at 200 mV applied voltage, for example, the MS-bio90 complex yielded a rate of $23.3 \pm 0.9$ s$^{-1}$, while the event rates of MS and bio90 individually were $0.09 \pm 0.04$ s$^{-1}$ and $1.1 \pm 0.2$ s$^{-1}$, respectively. In order to verify that the MS-bio90 events corresponded to actual translocations rather than stochastic interactions between the complex and the nanopore, polarity of the applied voltage was reversed during measurement and recapture events were observed.

Figure 2:
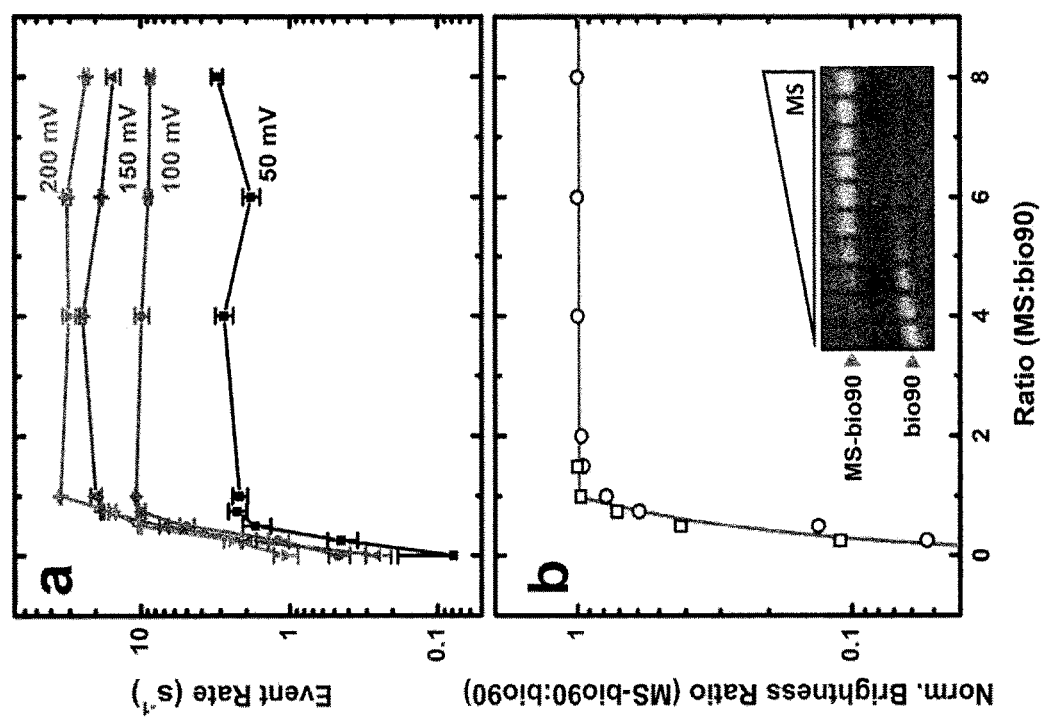
FIG. 2 illustrates complexed biological molecule translocation event rates at various electric field voltages in comparison to an electromobility shift assay over a common stoichiometric range according to some embodiments described herein.

In order to investigate the system further, a series of SS-nanopore measurements were performed in which MS was titrated against a constant amount (1 µM) of bio90. Over all investigated voltages, the measured event rate rose dramatically up to a molar ratio of 1:1 (FIG. 2a). However, from unity up to a molar ratio of 8:1 (MS:bio90), additional MS did not increase the event rate further. This was a result of the limited supply of ds-DNA needed to form nucleoprotein complexes; the protein had an extremely low off rate ($\sim 10^{-5}$ s$^{-1}$) and each oligonucleotide contained only a single biotin moiety, so it was expected that nearly all bio90 in solution was bound at or above an equimolar concentration. Comparing the translocation results to an electromobility shift assay (EMSA) performed with MS and bio90 over the same stoichiometric range, a strikingly similar trend was observed (FIG. 2b). These data supported the conclusion that virtually all observed translocation events for the admixture corresponded to MS-bio90 complexes. Additional evidence of the high specificity of this approach was provided by control measurements in which non-biotinylated dsDNA incubated with MS yielded a negligible event rate, equivalent to bio90 alone.

Figure 3:
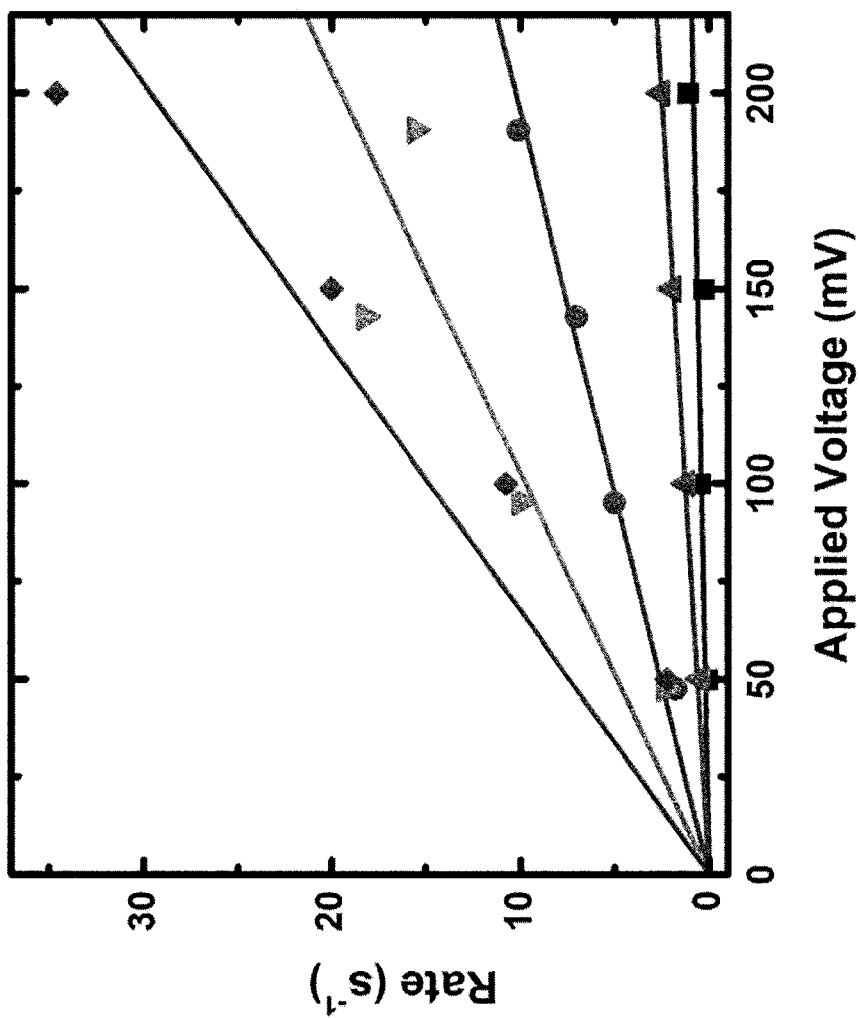
FIG. 3 illustrates complexed biological molecule event rates up to a molar ratio of 1:1 of translocating agent and complexed biological molecule according to one embodiment described herein.

Selective quantification of modified oligonucleotides: In FIG. 3, event rates up to a molar ratio of 1:1 were examined and a linear dependence on applied voltage was found. This implied that the capture process for the MS-bio90 complex was governed by diffusion rather than by interactions with the pore, in agreement with previous studies. Importantly, the observed trend offered a route to quantification of MS-bio90 complexes in solution as event frequency can vary with molecular concentration. Because nearly all events observed in the present system were attributed exclusively to the translocation of complexes, the linear fits in FIG. 3 link the concentration of MS-bio90 in solution to specific event rates produced at a given voltage. The measurements described thus far have been performed in a protein-limited regime (MS:bio90<1:1), and so the measured event rate facilitated quantification of MS-bio90 complexes in a background of unconjugated bio90. However, the same approach could in principal be used to quantify biotinylated oligonucleotides in a heterogeneous solution with non-biotinylated DNA as well.

Figure 4:
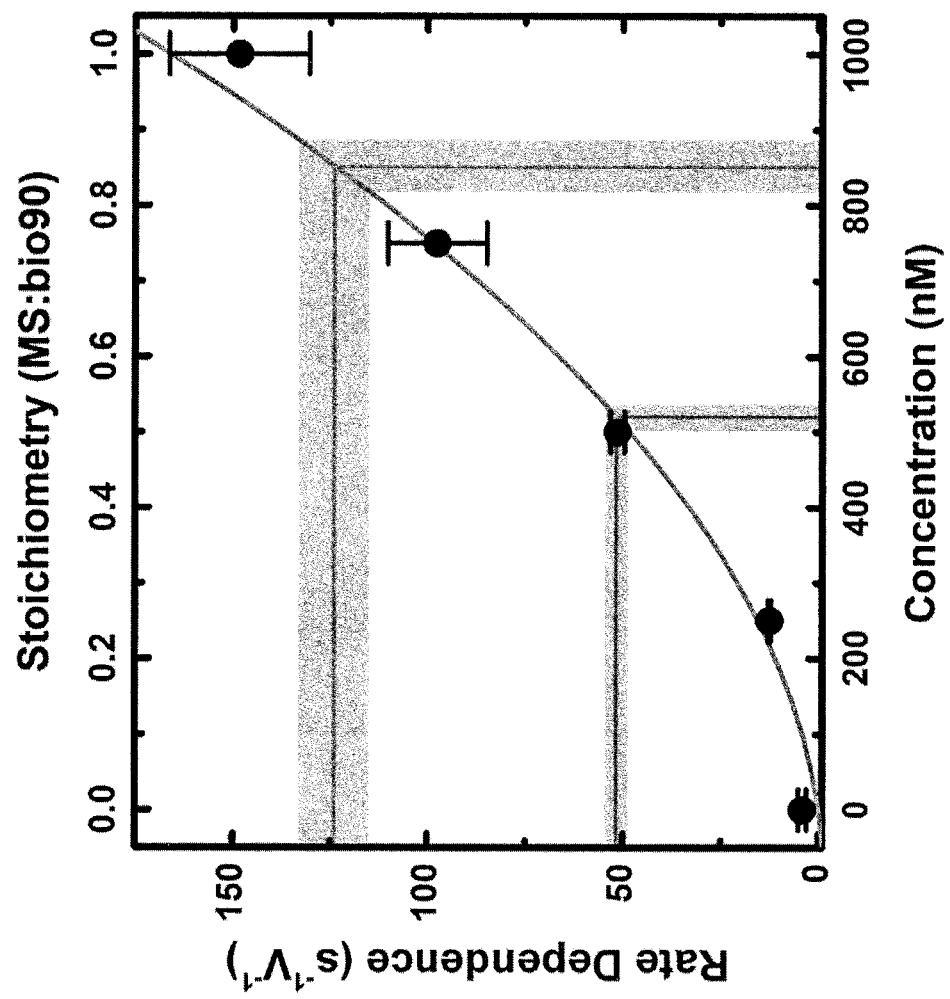
FIG. 4 illustrates quantification of complexed biological molecule concentration relative to translocation event rate according to one embodiment described herein.

To investigate this possibility, a blind test was conducted on two samples prepared by a third party. Each of these samples contained a different mixture of biotinylated and non-biotinylated 90 by ds-DNA mixed to a total concentration of 1 µM (equivalent to that of the measurements described above). To ensure that all bio90 was complexed, both solutions are incubated with MS at a concentration of 4 µM. As described in the previous sections, MS alone produced a negligible number of measurable events, and so excess protein did not perturb the measurements. SS-nanopore analysis revealed a linear relationship between applied voltage and event rate for both samples, as expected. Comparing the event rates obtained from the two blind samples to prior measurements (FIG. 4) derived a value for the bio90 concentration in each: $850 \pm 35$ nM in Sample 1 and $520 \pm 20$ nM in Sample 2. Remarkably, these experimentally-determined concentrations were in excellent agreement with the prepared values of 800±20 and 480±20 nM, respectively. These results demonstrate that our SS-nanopore approach is uniquely capable of quantifying DNA having single nucleotide biotin modifications selectively, even within a mixed sample.

Methods

SS-Nanopore Device Fabrication and Electrical Measurement

Nanopores were fabricated using a technique described elsewhere as in WO 2012/170499. Briefly, the beam of a scanning helium ion microscope (Carl Zeiss Orion Plus) was focused on a suspended silicon nitride thin film membrane (thickness 30 nm) in a silicon support chip. Calibrated exposure times were used to mill nanopores with diameters ranging from 7.3-7.7 nm. The support chip containing an individual pore was then positioned in a custom flow cell with fluid access to both sides of the membrane. Measurement solution (900 mM NaCl and 6 mM PBS buffer) was introduced on either side of the flow cell, and Ag/AgCl electrodes were immersed in the solution. Electrical measurements (Axopatch 200B) were used to verify that the device exhibited low RMS noise (typically <20 pA) and linear current-voltage characteristics that matched the calibrated nanopore diameter. Translocation measurements were performed by replacing the solution on one side of the device with measurement solution containing biomolecules. Conductance was recorded at a bandwidth of 200 kHz and filtered at 100 kHz with a four-pole Bessel filter. Analysis was performed with custom software with which we applied an additional low-pass filter of 25 kHz to all measurements. The event threshold for analysis was set at 4 standard deviations and only events with durations from 12-2000 µs were considered.

Biomolecules

Bio90 oligonucleotides were purchased (Integrated DNA Technologies, Coralville, Iowa) The opposing strand (forming the dsDNA) contained no modified nucleotides. The non-biotinylated oligonucleotide used in the mixture (blind measurements) had the same sequence but with no biotin moiety. The streptavidin variant employed (SAe1D3) contained one active biotin-binding site and was supplied by the Howarth lab (Oxford University). This mutant protein (54.5 kDa) retains binding affinity and stability similar to wild-type streptavidin and contains a hexaglutamate tag used for isolation that imparts a negative charge of −17.1e under comparable pH conditions.

Electrophoretic Mobility Shift Assay

MS was incubated with bio90 for 20 minutes at room temperature at molar ratios ranging from 0:1 to 8:1 (MS: bio90). The mixtures were then loaded onto a 1.5% agarose gel with ethidium bromide for visualization. The buffer reservoir of the electrophoresis unit was submerged in an ice bath to minimize dissociation of the protein-DNA complex.

Example 2

Selective Detection and Quantification Double-Stranded DNA

Figure 5:
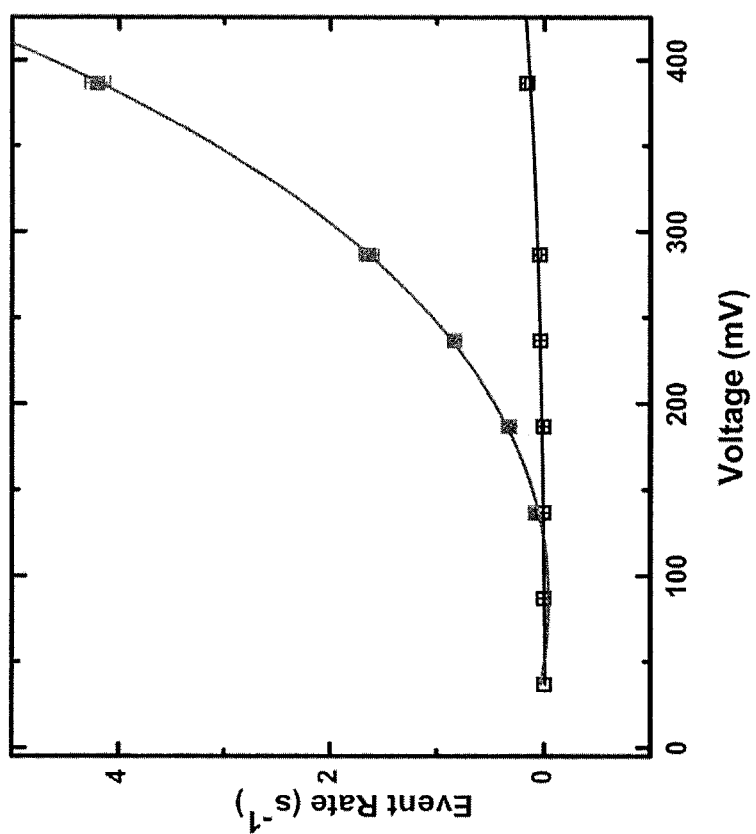
FIG. 5 illustrates translocation event rate versus applied voltage for complexed translocation agent and non-complexed translocation agent according to one embodiment described herein.
Figure 6:
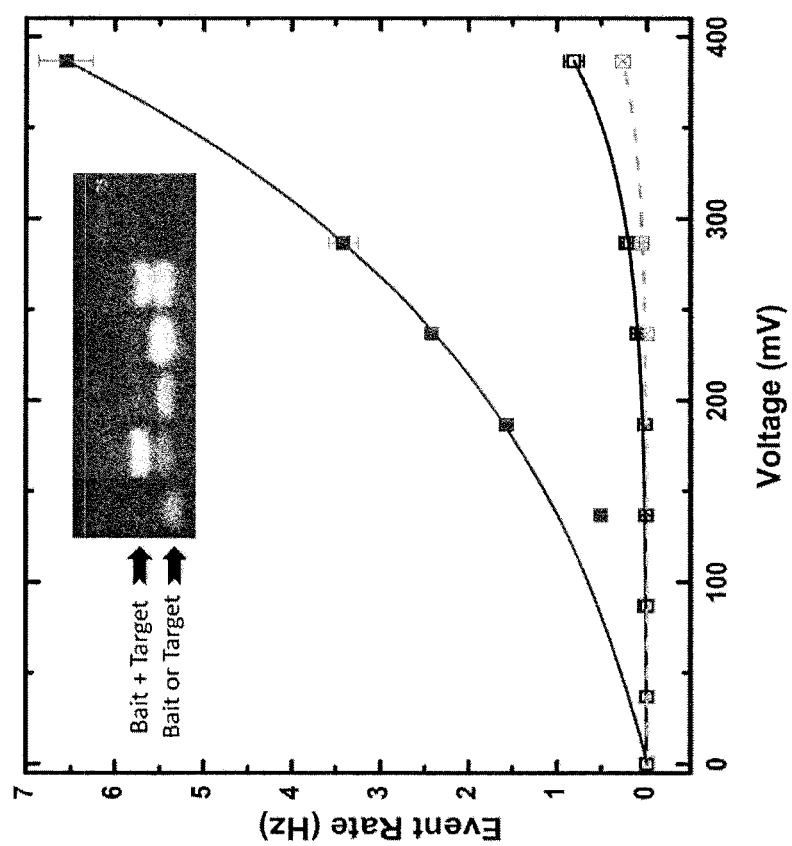
FIG. 6 illustrates translocation event rate versus applied voltage for complexed translocation agent, non-complexed translocation and uncomplexed single strand nucleic acid according to one embodiment described herein.

The ability to differentiate biotinylated forms of dsDNA and ssDNA due to variations in drag force imparted by the two types of DNA molecules was demonstrated. This effect was demonstrated by analyzing both single strand (ss) and double strand (ds) versions of 34 base pair (bp) monobiotinylated oligonucleotide by nanopore in the presence MS. A significant increase in event rate was observed for the dsDNA-MS, and no enhancement was observed for the ssDNA-MS as illustrated in FIG. 5. Based on this result, biotinylated ssDNA can be employed as a sequence specific translocating agent that can bind to its complimentary target sequence in a mixture of biological molecules. Sequence specific translocating capability of the 34 bp biotinylated ssDNA was tested on a mixture comprising single strand nucleic acid of homologous sequence and a background of four non-homologous ss-DNA sequences. MS was introduced into the mixture and thermal cycling was conducted to promote annealing. FIG. 6 illustrates the results where translocation of a hybridized complex of biotinylated dsDNA-MS was observed. Importantly, translocation of uncomplexed ss-DNA and uncomplexed biotinylated ss-DNA-MS translocating agent was not observed.

Example 3

Translocation Characterization of ds-DNA

Figure 7:
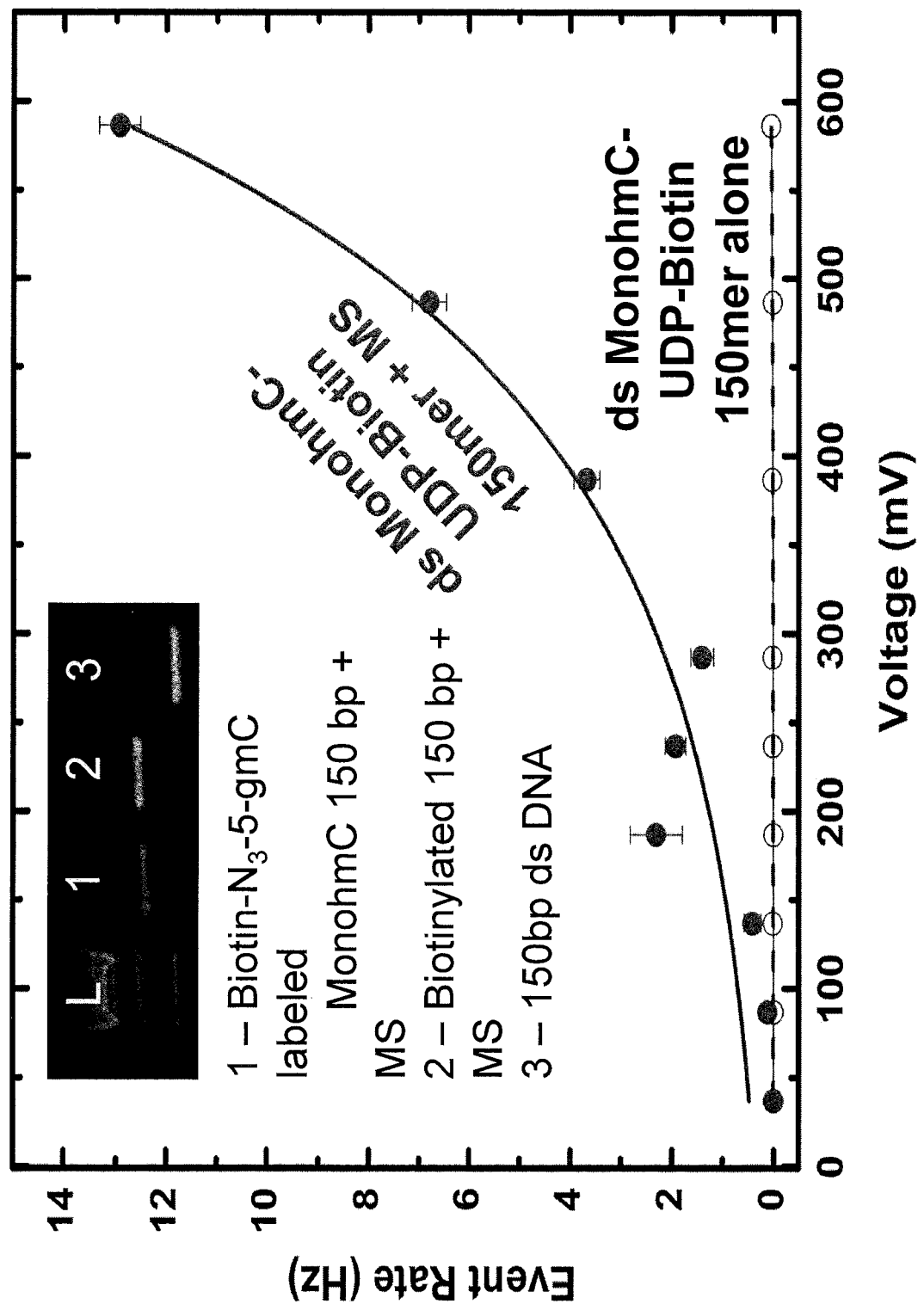
FIG. 7 illustrates translocation event rate versus applied voltage for complexed ds-DNA and non-complexed ds-DNA according to one embodiment described herein.
Figure 8:
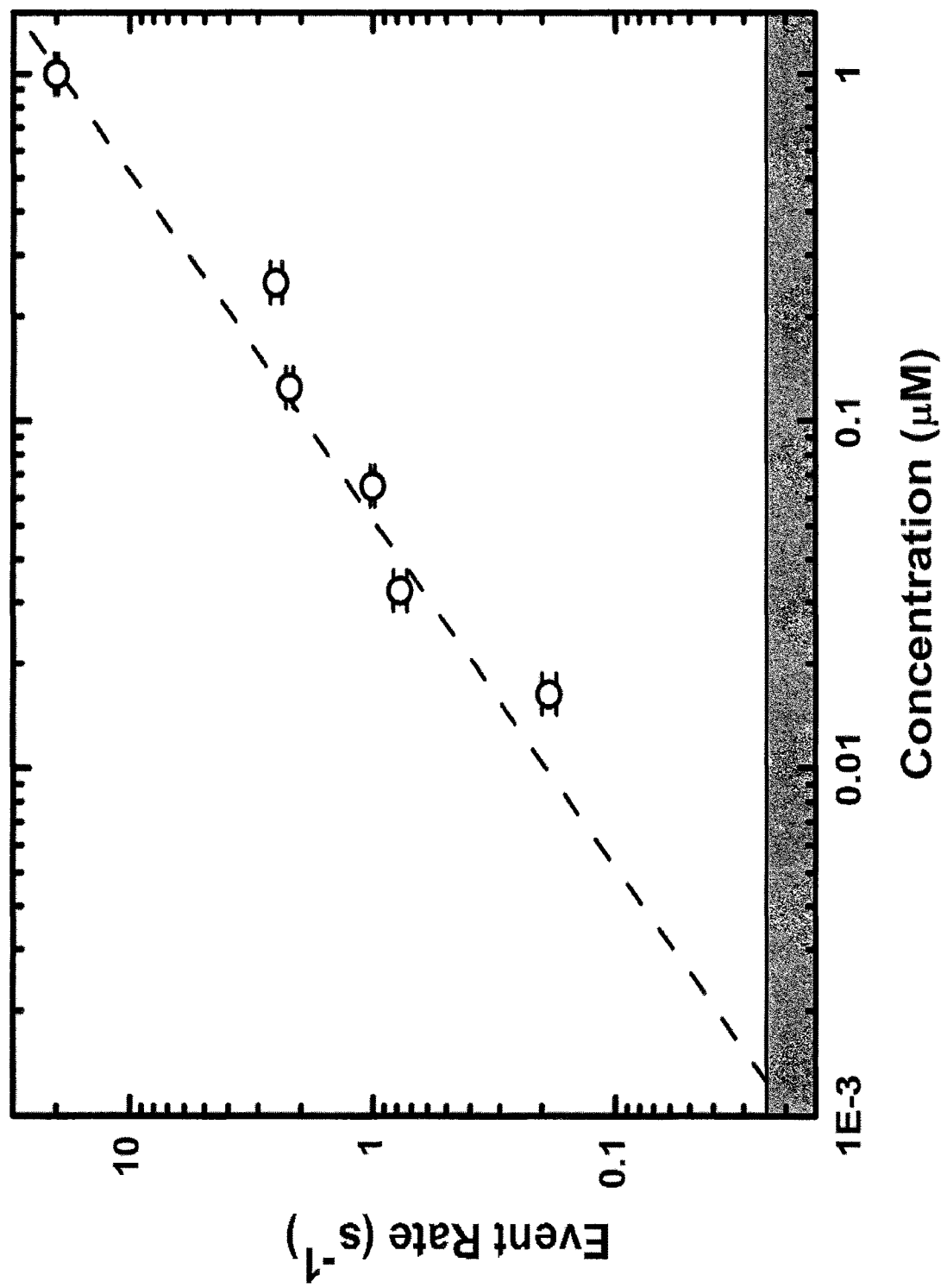
FIG. 8 illustrates translocation event rate relative to complexed biological molecule concentration according to one embodiment described herein.
Figure 9:
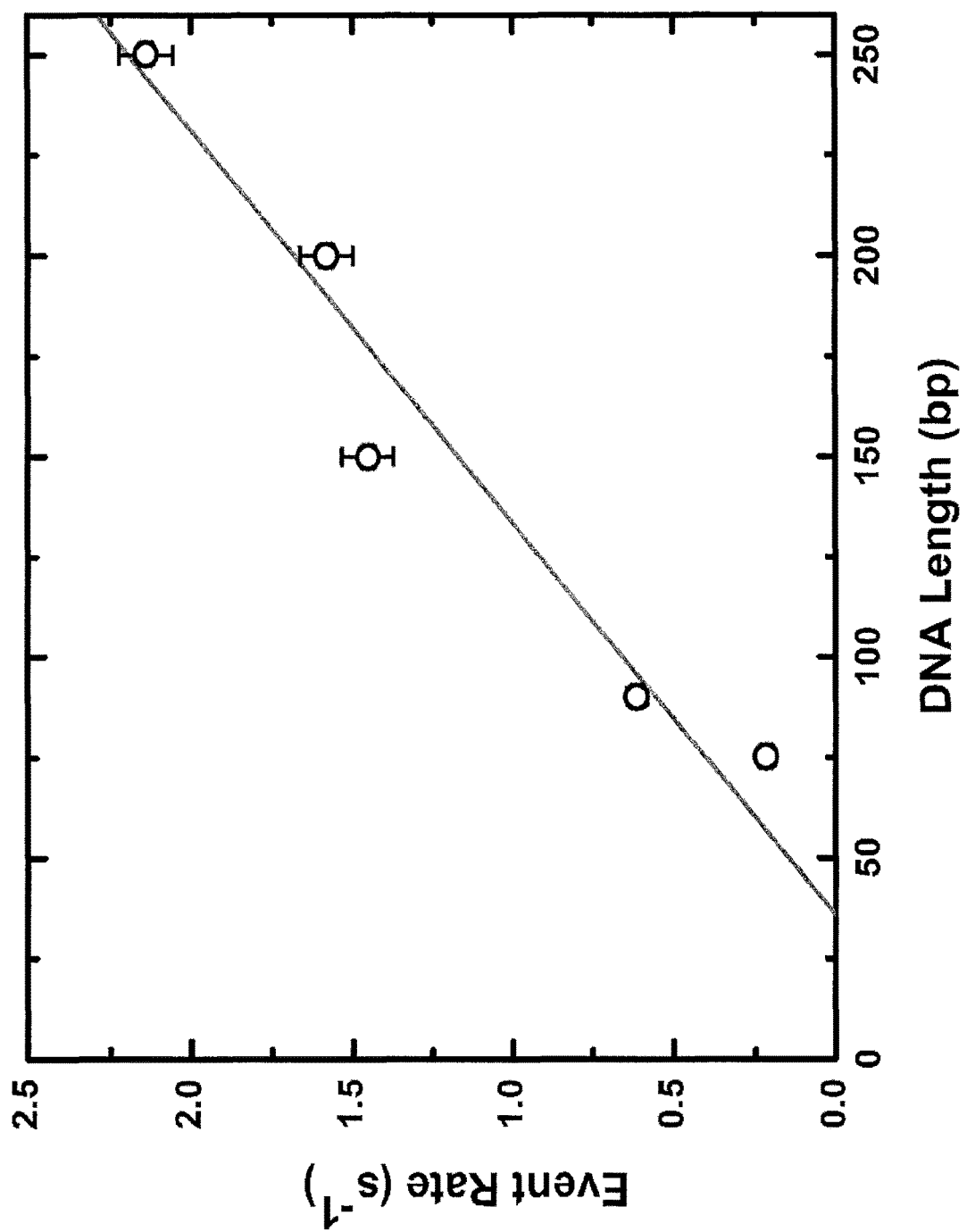
FIG. 9 illustrates translocation event rate relative to ds-DNA length according to one embodiment described herein.

A series of SS-nanopore measurements were performed in which translocation event rate of a 150 by ds-DNA strand having a single hydroxymethylcytosine enzymatically labeled with biotin and subsequently bound to MS was measured against nanopore applied voltage and concentration of the 150 by ds-DNA strand. Nanopore construction and operational parameters were consistent with those provided in Example 1 with the applied voltage ranging from 50-600 mV. FIG. 7 illustrates results of the testing where ds-DNA-biotin-MS translocation event rate increased with increasing voltage. For comparison, 150 by ds-DNA strand not employing the biotin-MS translocating agent architecture was tested and failed to register a translocation response. Translocation event rate dependency on ds-DNA-biotin-MS concentration was also explored. As illustrated in FIG. 8, translocation event rate varied generally linearly with ds-DNA-biotin-MS concentration at a constant applied voltage of 200 mV. The shaded portion of FIG. 8 represents the noise floor. Translocation event rate dependency on ds-DNA length was also investigated. As provided in FIG. 9, translocation rate exhibited substantially linear dependence on ds-DNA length. With these relationships established, methods described herein provide a powerful tool for characterization and quantification of biological molecules, including nucleic acids.

Various embodiments of the invention have been described in fulfillment of the various objects of the invention. It should be recognized that these embodiments are merely illustrative of the principles of the present invention. Numerous modifications and adaptations will be readily apparent to those skilled in the art without departing from the spirit and scope of the invention.

The invention claimed is:

1. A method of biological molecule composition analysis comprising:
    providing a mixture comprising non-complexed biological molecules;
    providing a membrane comprising at least one nanopore, and setting conditions of nanopore operation to translocate the non-complexed biological molecules through the at least one nanopore without generating detectable changes in nanopore electrical current;
    adding a translocating agent to the mixture and selectively binding biological molecules of the mixture to provide biological molecules complexed with the translocating agent in addition to the non-complexed biological molecules;

contacting the mixture with the membrane comprising the at least one nanopore;

translocating the complexed biological molecules through the at least one nanopore;

detecting the translocation of the complexed biological molecules via changes in nanopore electrical current, wherein translocation of the non-complexed biological molecules is not detected via the changes in nanopore electrical current.

2. The method of claim 1 further comprising measuring the rate of translocation events of the complexed biological molecules.

3. The method of claim 2 further comprising determining concentration of the complexed biological molecules from the rate of translocation events.

4. The method of claim 3, wherein the concentration of the complexed biological molecules exhibits a substantially linear relationship with the rate of translocation events.

5. The method of claim 1 further comprising recovering the translocated complexed biological molecules.

6. The method of claim 1, wherein the translocating agent is a chemical species of sufficient charge to permit translocation detection of the complexed biological molecules under the conditions of nanopore operation.

7. The method of claim 1, wherein the biological molecules complexed with a translocating agent and non-complexed biological molecules are independently selected from the group consisting of nucleic acids and proteins.

8. The method of claim 1, wherein the translocating agent comprises a single strand nucleic acid modified with an affinity tag for binding one or more molecular species prior to translocation of the complexed biological molecules.

9. The method of claim 8, wherein the affinity tag binds one or more proteins.

10. The method of claim 9, wherein the affinity tag comprises biotin or a derivative thereof.

11. The method of claim 8, wherein the biological molecules complexed with the translocating agent are single strand nucleic acids having sequence complimentary to the translocating agent.

12. The method of claim 11, wherein the single strand nucleic acids comprise one or more types of RNA.

13. The method of claim 1, wherein the complexed biological molecules are nucleic acids and the rate of the translocation events varies linearly with length of the nucleic acids.

14. The method of claim 1, wherein the at least one nanopore has a diameter of 5 to 30 nm.

15. The method of claim 1, wherein the at least one nanopore has a diameter of 10 to 20 nm.

16. The method of claim 1, wherein the conditions of nanopore operation comprise an electrical field set by an applied voltage of 1 mV to 5V.

17. The method of claim 1, wherein the translocating agent is a nanoparticle.

18. The method of claim 1, wherein the complexed biological molecules are double-stranded DNA.

19. The method of claim 1, wherein the translocating agent is a chemical species of sufficient size or size and charge to permit translocation detection of the complexed biological molecules under the conditions of nanopore operation.

* * * * *